United States Patent
Leyshon

(10) Patent No.: US 10,513,472 B2
(45) Date of Patent: Dec. 24, 2019

(54) METHODS OF PRODUCING PROPYLENE AND ETHYLENE

(71) Applicant: Lyondell Chemical Technology, L.P., Houston, TX (US)

(72) Inventor: David W. Leyshon, Houston, TX (US)

(73) Assignee: Lyondell Chemical Technology, L.P., Houston, TX (US)

( * ) Notice: Subject to any disclaimer, the term of this patent is extended or adjusted under 35 U.S.C. 154(b) by 0 days.

(21) Appl. No.: 16/165,603

(22) Filed: Oct. 19, 2018

(65) Prior Publication Data

US 2019/0127291 A1 May 2, 2019

Related U.S. Application Data

(60) Provisional application No. 62/577,525, filed on Oct. 26, 2017.

(51) Int. Cl.
  *C07C 1/22* (2006.01)
  *B01J 21/16* (2006.01)
  *B01J 29/85* (2006.01)

(52) U.S. Cl.
  CPC .............. *C07C 1/22* (2013.01); *B01J 21/16* (2013.01); *B01J 29/85* (2013.01); *C07C 2529/40* (2013.01); *C07C 2529/82* (2013.01)

(58) Field of Classification Search
  CPC .... C07C 4/06; C07C 7/04; C07C 7/02; C07C 4/02; C07C 1/20; C07C 11/02
  See application file for complete search history.

(56) References Cited

U.S. PATENT DOCUMENTS

| 4,062,905 A * | 12/1977 | Chang ................... C07C 1/20 585/640 |
| 5,107,042 A | 4/1992 | Gaffney et al. |
| 5,171,921 A | 12/1992 | Gaffney et al. |
| 9,254,479 B2 * | 2/2016 | Ryu .................... B01J 21/12 |
| 2012/0041243 A1 * | 2/2012 | Senetar .................. C07C 1/20 585/251 |
| 2013/0237713 A1 | 9/2013 | Chewter et al. |
| 2013/0237714 A1 * | 9/2013 | Sadasivan Vijayakumari ............ C07C 1/20 549/523 |

FOREIGN PATENT DOCUMENTS

| WO | WO93/21139 | * 10/1993 | ............... C07C 1/20 |
| WO | 2013034677 A1 | 3/2013 | |

OTHER PUBLICATIONS

The International Search Report and Written Opinion for PCT/US2018/056727 dated Feb. 5, 2019.

* cited by examiner

*Primary Examiner* — Youngsul Jeong

(57) ABSTRACT

Methods of producing at least one of ethylene and propylene. The methods may include contacting a mixture of C4+ compounds with a catalyst to convert at least a portion of the C4+ compounds to at least one of ethylene and propylene. The catalyst can include a phosphorus treated zeolite, and the mixture of C4+ compounds can include at least one of t-butyl alcohol and methyl t-butyl ether.

18 Claims, No Drawings

METHODS OF PRODUCING PROPYLENE AND ETHYLENE

CROSS-REFERENCE TO RELATED APPLICATIONS

This application claims the benefit of priority to U.S. Provisional Application No. 62/577,525, filed on Oct. 26, 2017, which is incorporated herein by reference in its entirety.

BACKGROUND OF THE INVENTION

Methods are known for producing commercially important olefins, such as ethylene and propylene. Such methods include steam cracking, propane dehydrogenation, and various refinery catalytic cracking operations. Each of these procedures has one or more disadvantages. For example, propylene yields from steam cracking typically are not very high, and usually are not substantially improved by recycling. Also, purification of non-propylene products may be required, which can be costly, and such products usually have only fuel value. Propane dehydrogenation processes usually are characterized by rapid catalyst coking, which can require frequent, costly regenerations. Also, reasonable conversions typically require sub-atmospheric pressures, and propane can be difficult to separate from propylene. Moreover, propylene supplies from catalytic conversions are uncertain, and transportation and/or purification can present problems.

Also, many current chemical processes produce t-butyl alcohol and/or methyl t-butyl ether as side products.

Therefore, methods are desired that convert t-butyl alcohol and/or methyl t-butyl ether to ethylene and/or propylene, especially methods that do so in an efficient, cost-effective, and/or facile process.

SUMMARY OF THE INVENTION

Provided herein are methods of producing at least one of ethylene and propylene. In embodiments, the methods comprise providing a first mixture of C4+ compounds; and contacting the first mixture of C4+ compounds with a catalyst comprising a phosphorus treated zeolite to convert at least a portion of the first mixture of C4+ compounds to at least one of ethylene and propylene. The first mixture of C4+ compounds may include at least one of t-butyl alcohol and methyl t-butyl ether. In one embodiment, the methods further comprise separating the ethylene and/or the propylene from the first mixture of C4+ compounds to form a second mixture of C4+ compounds, and contacting the second mixture of C4+ compounds with the catalyst to convert at least a portion of the second mixture of C4+ compounds to at least one of ethylene and propylene. In another embodiment, the methods further comprise contacting the first mixture of C4+ compounds comprising at least one of t-butyl alcohol and methyl t-butyl ether with the catalyst.

DETAILED DESCRIPTION OF THE INVENTION

Provided herein are methods for producing at least one of ethylene and propylene from a mixture of C4+ compounds that overcome one or more of the disadvantages associated with other methods for producing commercially important olefins.

The mixture of C4+ compounds may be contacted with a catalyst comprising a phosphorus treated zeolite to convert at least a portion of the mixture of C4+ compounds to at least one of ethylene and propylene. The ethylene and/or propylene then may be separated from the mixture of C4+ compounds, and the mixture of C4+ compounds may be contacted with the catalyst a second time. In addition to the ethylene and/or propylene, other, non-C4+ compounds, including, but not limited to, coke, $C_2H_6$, and $C_3H_8$, may be removed from the mixture after one or more of the contacting steps. Alternatively, the mixture of C4+ compounds may be contacted with the catalyst a second time without removing ethylene and/or propylene from the mixture. The contacting step may be repeated any number of times. In one embodiment, the contacting step is repeated until a desired conversion rate of the mixture of C4+ compounds, or a portion thereof, to at least one of propylene and ethylene is achieved.

Generally, the mixture of C4+ compounds may be contacted with a catalyst comprising phosphorus treated zeolite at any combination of temperature and pressure that is effective to convert at least a portion of the mixture of C4+ compounds to at least one of ethylene and propylene. In one embodiment, the contacting occurs at a temperature of about 600° F. to about 1,200° F. In another embodiment, the contacting occurs at a temperature of about 700° F. to about 1,050° F. In a further embodiment, the contacting occurs at a temperature of about 700° F. to about 950° F. In yet another embodiment, the contacting occurs at a temperature of about 700° F. to about 850° F. In a still further embodiment, the contacting occurs at a temperature of about 700° F. to about 750° F. In additional embodiments, the contacting occurs at a temperature of about 800° F. to about 1,050° F. In some embodiments, the contacting occurs at a temperature of about 900° F. to about 1,050° F. In further embodiments, the contacting occurs at a temperature of about 1,000° F. to about 1,050° F.

In one embodiment, the contacting occurs at ambient pressure. In another embodiment, the contacting occurs at a pressure of about 1 psig to about 20 psig. In yet another embodiment, the contacting occurs at a pressure of about 5 psig to about 15 psig. In a still further embodiment, the contacting occurs at a pressure of about 8 psig to about 12 psig. In an additional embodiment, the contacting occurs at a pressure of about 10 psig.

In one embodiment, the contacting occurs at a temperature of about 600° F. to about 1,200° F., about 700° F. to about 1,050° F., about 700° F. to about 950° F., about 700° F. to about 850° F., about 700° F. to about 750° F., about 800° F. to about 1,050° F., about 900° F. to about 1,050° F., or about 1,000° F. to about 1,050° F., and at ambient pressure.

In one embodiment, the contacting occurs at a temperature of about 600° F. to about 1,200° F., about 700° F. to about 1,050° F., about 700° F. to about 950° F., about 700° F. to about 850° F., about 700° F. to about 750° F., about 800° F. to about 1,050° F., about 900° F. to about 1,050° F., or about 1,000° F. to about 1,050° F., and a pressure of about 1 psig to about 20 psig.

In one embodiment, the contacting occurs at a temperature of about 600° F. to about 1,200° F., about 700° F. to about 1,050° F., about 700° F. to about 950° F., about 700° F. to about 850° F., about 700° F. to about 750° F., about 800° F. to about 1,050° F., about 900° F. to about 1,050° F., or about 1,000° F. to about 1,050° F., and a pressure of about 5 psig to about 15 psig.

In one embodiment, the contacting occurs at a temperature of about 600° F. to about 1,200° F., about 700° F. to about 1,050° F., about 700° F. to about 950° F., about 700° F. to about 850° F., about 700° F. to about 750° F., about 800° F. to about 1,050° F., about 900° F. to about 1,050° F., or about 1,000° F. to about 1,050° F., and a pressure of about 8 psig to about 12 psig.

In one embodiment, the contacting occurs at a temperature of about 600° F. to about 1,200° F., about 700° F. to about 1,050° F., about 700° F. to about 950° F., about 700° F. to about 850° F., about 700° F. to about 750° F., about 800° F. to about 1,050° F., about 900° F. to about 1,050° F., or about 1,000° F. to about 1,050° F., and a pressure of about 10 psig.

The hydrocarbon feed weight hourly space velocity (based on the zeolite component of the catalyst) may be about 1 to about 750 $hr^{-1}$, about 1 to about 500 $hr^{-1}$, about 1 to about 400 $hr^{-1}$, about 200 to about 400 $hr^{-1}$, about 300 to about 400 $hr^{-1}$, or about 316 $hr^{-1}$.

Mixture of C4+ Compounds

In embodiments, the mixture of C4+ compounds comprises at least one of t-butyl alcohol and methyl t-butyl ether. In one embodiment, the mixture of C4+ compounds comprises t-butyl alcohol. In another embodiment, the mixture of C4+ compounds comprises methyl t-butyl ether. In yet another embodiment, the mixture of C4+ compounds comprises methyl t-butyl ether and t-butyl alcohol.

The mixture of C4+ compounds may be a tailstream, or part of a tailstream, of a chemical process, such as a methanol-to-olefin process.

The mixture of C4+ compounds may be part of a feed stream that includes a diluent. The diluent, in embodiments, is present in the feed stream in an amount of about 10% to about 40% by weight of the mixture of C4+ compounds, about 15% to about 35% by weight of the C4+ compounds, about 20% to about 35% by weight of the C4+ compounds, about 25% to about 35% by weight of the C4+ compounds, or about 30% by weight of the mixture of C4+ compounds. In one embodiment, the diluent comprises steam.

Conversion Rates

Unless otherwise noted, the "conversion rates" provided herein are those obtained after a contacting step, as described herein, is performed once, and the contact step may be the first contacting step, second contacting step, etc. Higher cumulative conversion rates may be achieved by repeating the contacting step one or more times, as described herein.

In embodiments, the mixture of C4+ compounds comprises t-butyl alcohol, and the weight percentage of the t-butyl alcohol converted to ethylene is about 2 to about 50, about 2 to about 40, about 2 to about 30, 2 to about 20, about 2 to about 15, about 2 to about 10, about 2 to about 8, about 2 to about 6, or about 4 to about 6, or about 4 to about 5.

In embodiments, the mixture of C4+ compounds comprises t-butyl alcohol, and the weight percentage of the t-butyl alcohol converted to propylene is about 10 to about 50, about 10 to about 40, about 10 to about 30, about 15 to about 30, about 15 to about 25, about 20 to about 25, or about 22 to about 24.

In embodiments, the mixture of C4+ compounds comprises t-butyl alcohol, and the weight percentage of the t-butyl alcohol converted to at least one of propylene and ethylene is about 15 to about 60, about 15 to about 50, about 15 to about 40, about 20 to about 40, about 20 to about 35, about 20 to about 30, or about 25 to about 30.

In embodiments, the mixture of C4+ compounds comprises methyl t-butyl ether, and the weight percentage of the methyl t-butyl ether converted to ethylene is about 2 to about 50, about 2 to about 40, about 2 to about 30, 2 to about 20, about 2 to about 15, about 2 to about 10, about 2 to about 8, about 2 to about 6, or about 4 to about 6, or about 4 to about 5.

In embodiments, the mixture of C4+ compounds comprises methyl t-butyl ether, and the weight percentage of the methyl t-butyl ether converted to propylene is about 10 to about 50, about 10 to about 40, about 10 to about 30, about 15 to about 30, about 15 to about 25, about 20 to about 25, or about 22 to about 24.

In embodiments, the mixture of C4+ compounds comprises methyl t-butyl ether, and the weight percentage of the methyl t-butyl ether converted to at least one of propylene and ethylene is about 15 to about 60, about 15 to about 50, about 15 to about 40, about 20 to about 40, about 20 to about 35, about 20 to about 30, or about 25 to about 30.

In embodiments, the mixture of C4+ compounds comprises t-butyl alcohol, and at least 20 weight %, at least 22 weight %, at least 25 weight %, at least 30 weight %, at least 35 weight %, at least 40 weight %, at least 45 weight %, or at least 50% of the t-butyl alcohol is converted to at least one of ethylene and propylene.

In embodiments, the mixture of C4+ compounds comprises t-butyl alcohol, and at least 20 weight %, at least 22 weight %, at least 25 weight %, at least 30 weight %, at least 35 weight %, at least 40 weight %, at least 45 weight %, or at least 50% of the t-butyl alcohol is converted to propylene.

In embodiments, the mixture of C4+ compounds comprises t-butyl alcohol, and at least 2 weight %, at least 5 weight %, at least 10 weight %, at least 20 weight %, at least 25 weight %, at least 30 weight %, at least 40 weight %, or at least 50% of the t-butyl alcohol is converted to ethylene.

In embodiments, the mixture of C4+ compounds comprises methyl t-butyl ether, and at least 20 weight %, at least 22 weight %, at least 25 weight %, at least 30 weight %, at least 35 weight %, at least 40 weight %, at least 45 weight %, or at least 50% of the methyl t-butyl ether is converted to at least one of ethylene and propylene.

In embodiments, the mixture of C4+ compounds comprises methyl t-butyl ether, and at least 10 weight %, at least 20 weight %, at least 25 weight %, at least 30 weight %, at least 35 weight %, at least 40 weight %, at least 45 weight %, or at least 50% of the methyl t-butyl ether is converted to propylene.

In embodiments, the mixture of C4+ compounds comprises methyl t-butyl ether, and at least 2 weight %, at least 5 weight %, at least 10 weight %, at least 20 weight %, at least 35 weight %, at least 40 weight %, at least 45 weight %, or at least 50% of the methyl t-butyl ether is converted to ethylene.

Catalysts

Generally, the catalysts provided herein include phosphorus treated zeolite catalysts. In embodiments, the phosphorus treated zeolite comprises phosphorus in an amount of about 0.1% to about 10%, by weight of the zeolite, about 0.1% to about 8%, by weight of the zeolite, about 0.1% to about 6%, by weight of the zeolite, about 0.1% to about 5% by weight of the zeolite, about 1% to about 4%, by weight of the zeolite, about 1% to about 3%, by weight of the zeolite, or about 1.2%, by weight of the zeolite.

The phosphorus treated zeolite may be made by contacting a zeolite, which may a powder, with a phosphorus containing compound. The phosphorus containing compound may be an acid. Examples of phosphorus containing compounds include, but are not limited to, $H_3PO_4$, ammonium hydrogen phosphates, such as $(NH_4)_2HPO_4$ or $(NH_4)$ $H_2PO_4$, phosphonic acid (also called phosphorus acid) $H_3PO_3$, phosphorus pentoxide ($P_2O_5$), or a combination thereof. The zeolite may be contacted with the phosphorus containing compound in an amount sufficient to impart the catalyst with a desired phosphorus content. The zeolite may be contacted with water before, during, or after the zeolite is contacted with the phosphorus containing compound. The amount of water may be an amount sufficient to wet the zeolite only. After being contacted with a phosphorus containing compound and/or water, the zeolite may be dried by any means known in the art.

The phosphorus treated zeolite may be combined with a binder. The binder may include silica, kaolin, calcium, bentonite, alumina, silica aluminate, or a combination thereof. In one embodiment, the binder includes bentonite clay, silica, and kaolin. The bentonite clay, silica, and kaolin may be present in the binder at a bentonite clay:silica:kaolin weight ratio of about 1:(8-16):(20-28); about 1:(10-14):(22-26); or about 1:12:24.

The phosphorus treated zeolite, in embodiments, is present in the catalyst in an amount of about 1% to about 50% by weight, based on the combined weight of the phosphorus treated zeolite and the binder. In further embodiments, the phosphorus treated zeolite is present in the catalyst in an amount of about 5% to about 40% by weight, based on the combined weight of the phosphorus treated zeolite and the binder. In additional embodiments, the phosphorus treated zeolite is present in the catalyst in an amount of about 5% to about 30% by weight, based on the combined weight of the phosphorus treated zeolite and the binder. In a particular embodiment, the phosphorus treated zeolite is present in the catalyst in an amount of about 10% to about 25% by weight, based on the combined weight of the phosphorus treated zeolite and the binder. In some embodiments, the phosphorus treated zeolite is present in the catalyst in an amount of about 15% to about 30% by weight, based on the combined weight of the phosphorus treated zeolite and the binder. In particular embodiments, the phosphorus treated zeolite is present in the catalyst in an amount of about 20% to about 30% by weight, based on the combined weight of the phosphorus treated zeolite and the binder. In one embodiment, the phosphorus treated zeolite is present in the catalyst in an amount of about 25% by weight, based on the combined weight of the phosphorus treated zeolite and the binder.

The phosphorus treated zeolite and binder may be contacted with an amount of water sufficient to form a paste, and the paste may be mixed by any means known in the art in order to form a paste that is at least substantially homogeneous.

The at least substantially homogeneous paste may be extruded into extrudates of any desired size. The extrudates also may be calcined, steamed, or a combination thereof. The calcining may be performed at a temperature of about 500° C. to about 700° C., or about 600° C. The steam treatment, in one embodiment, is conducted prior to contacting the catalyst with a mixture of C4+ hydrocarbons. The steam treatment may be performed at a temperature of about 800° F. to about 1200° F., 500° C. to 700° C., or about 550° C. to about 600° C., and at a pressure of about 1 to about 5 atmospheres, or about 1.5 to about 3 atmospheres, for about 1 to about 48 hours, or about 15 to about 30 hours.

The extrudates generally may have any desired size. For lab testing, the extrudates may have a size of 6 to 20 mesh. In one embodiment, the catalyst is a fixed bed catalyst, and the extrudates are particles having an average diameter of about 2 mm to 5 mm. The particles may be at least substantially spherical, but the use of the term "diameter" is not intended to convey that the particles necessarily are or include at least substantially spherical particles. When particles are not at least substantially spherical, the term "diameter" refers to the average largest dimension of particles.

The term "zeolite", as used herein, generally refers to porous materials, such as hydrated, crystalline metal aluminosilicates, and/or molecular sieves of a non-zeolitic material. Thus, zeolites include a group of natural or synthetic hydrated aluminosilicate minerals that contain alkali and alkaline metals. Zeolites may be characterized by a framework structure that encloses interconnected cavities occupied by ion-exchangeable large metal cations, such as potassium and water molecules permitting reversible dehydration.

In embodiments, the zeolite comprises a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms may be equal to about 2. The framework may exhibit a negative electrovalence that can be balanced by the inclusion of cations within the crystal. The cations may include potassium cations, ammonium cations, or a combination thereof.

The formula of the zeolite may vary without changing the crystalline structure. In an embodiment, the mole ratio of silicon dioxide to aluminum oxide ($SiO_2/Al_2O_3$) in the zeolite may vary from about 10 to about 200. In one embodiment, the molar $SiO_2:Al_2O_3$ ratio is about 20 to about 60.

In one embodiment, the zeolite has an alkali metal content of less than about 0.5% by weight of the zeolite. Alkali metals are those in Group IA or Group IIA of the periodic table, such as lithium, sodium, potassium, calcium, etc.

In embodiments, the zeolite is selected from ZSM-5, ZSM-11, ZSM-22, ZSM-23, ZSM-35, ZSM-48, ZSM-57, SUZ-4, SSZ-23; SSZ-25; SSZ-28, SSZ-32, SSZ-36, ZSM-3, ZSM-4, ZSM-10, ZSM-12, ZSM-20, zeolite beta, zeolite omega, zeolite L, zeolite X, zeolite Y, REY, USY, RE-USY, mordenite, LZ-210, LZ-210-M, LZ-210-T, LZ-210-A, SSZ-24, SSZ-26, SSZ-31, SSZ-33, SSZ-35, SSZ-37, SSZ-41, SSZ-42, SSZ-44, MCM-58, or a combination thereof. In one embodiment, the zeolite is ZSM-5.

In embodiments, the catalyst comprises a phosphorus treated ZSM-5 zeolite. In one embodiment, the catalyst comprises a phosphorus treated ZSM-5 zeolite having a molar $SiO_2:Al_2O_3$ ratio of about 20 to about 60. In another embodiment, the catalyst comprises a phosphorus treated ZSM-5 zeolite having an alkali metal content of less than about 0.5% by weight of the ZSM-5 zeolite.

In embodiments, the catalyst is a fixed bed catalyst. In another embodiment, the catalyst is a liquid catalyst.

EXAMPLES

The present invention is further illustrated by the following examples, which are not to be construed in any way as imposing limitations upon the scope thereof. On the contrary, it is to be clearly understood that resort may be had to various other aspects, embodiments, modifications, and equivalents thereof which, after reading the description herein, may suggest themselves to one of ordinary skill in the art without departing from the spirit of the present invention or the scope of the appended claims. Thus, other aspects of this invention will be apparent to those skilled in the art from consideration of the specification and practice of the invention disclosed herein.

Example 1—Preparation of Catalyst To 200 g of CBV5524G zeolite powder (Zeolyst, USA), $H_3PO_4$ and water were added. The $H_3PO_4$ was added in an amount sufficient to provide an equivalent of 1.2% by weight phosphorus, based on the weight of the dry zeolite powder. Water was added in an amount sufficient to wet the powder barely (incipient wetness). The zeolite powder was then dried overnight at 120° C.

To the zeolite powder was added 16 g of bentonite clay, 202 g of Davison 633 silica gel (VWR, USA), 388 g of kaolin, and an amount of DI water sufficient to make a viscous paste. These components were then mixed with a mixer (Caleva) to form a homogeneous paste.

The paste was then extruded into 2 mm OD extrudates with a high torque extruder (Bonnot BA373). The extrudates were then calcined at 600° C. in air, and then steamed for 24 hours at 575° C.

Example 2—Conversion of t-Butyl Alcohol

The catalyst of Example 1 was configured as a fixed bed catalyst through which vaporized t-butyl alcohol (TBA) was fed at 1 atm, 1050° F., and a weight hourly space velocity of 316 $hr^{-1}$.

The conversion of the TBA was 99.8%, and the product selectivities are shown it the following table:

TABLE 1

Product Selectivity of Example 2

| Component | Selectivity (g/100 g TBA converted) |
|---|---|
| Coke | 0.06 |
| $CO_2$ | 0.03 |
| $H_2$ | 0.02 |
| $CH_4$ | 0.08 |
| $C_2H_4$ | 4.73 |
| $C_2H_6$ | 0.07 |
| $C_3H_6$ | 22.57 |
| $C_3H_8$ | 1.48 |
| Isobutane | 1.48 |
| n-Butane | 1.03 |
| C4 olefins | 51.98 |
| C5 olefins | 11.12 |
| C5 paraffins | 0.85 |
| C6+ | 4.5 |

The C4+ products, including isobutane, n-butane, C4 olefins, C5 olefins, C5 paraffins, and C6+ products, then may be recycled to produce more ethylene and/or propylene.

What is claimed is:

1. A method of producing at least one of ethylene and propylene, the method comprising:
   providing a first mixture of C4+ compounds; and
   contacting the first mixture of C4+ compounds with a catalyst comprising:
   (a) a phosphorus treated zeolite, wherein the phosphorus treated zeolite comprises an alkali metal, and wherein the alkali metal is present in an amount no greater than about 0.5% by weight of the phosphorus treated zeolite, and
   (b) a binder, wherein the binder comprises bentonite clay, silica and kaolin and wherein the bentonite clay, silica and kaolin are present in the binder in a bentonite clay:silica:kaolin weight ratio of about 1:8-16:20,
   to convert at least a portion of the first mixture of C4+ compounds to at least one of ethylene and propylene, thereby producing a first effluent comprising at least one of ethylene and propylene
   wherein the first mixture of C4+ compounds comprises at least one of t-butyl alcohol and methyl t-butyl ether.

2. The method of claim 1, further comprising separating the ethylene and/or the propylene from the first effluent to form a second mixture of C4+ compounds, and contacting the second mixture of C4+ compounds with the catalyst to convert at least a portion of the second mixture of C4+ compounds to at least one of ethylene and propylene.

3. The method of claim 1 wherein the first mixture of C4+ compounds comprises the t-butyl alcohol, and at least 20 weight % of the t-butyl alcohol is converted to at least one of ethylene and propylene.

4. The method of claim 3, wherein at least 22 weight % of the t-butyl alcohol is converted to propylene.

5. The method of claim 1 wherein the first mixture of C4+ compounds comprises the methyl t-butyl ether, and at least 20 weight % of the methyl t-butyl ether is converted to at least one of ethylene and propylene.

6. The method of claim 5, wherein at least 22 weight % of the methyl t-butyl ether is converted to propylene.

7. The method of claim 1 wherein the phosphorus treated zeolite comprises a ZSM-5 zeolite.

8. The method of claim 7, wherein the ZSM-5 zeolite has an alkali metal content of about 0.5% by weight of the ZSM-5 zeolite.

9. The method of claim 1 wherein the phosphorus treated zeolite comprises phosphorus in an amount of about 0.1% to about 10% by weight of the phosphorus treated zeolite.

10. The method of claim 1 wherein the phosphorus treated zeolite comprises phosphorus in an amount of about 1% to about 3% by weight of the phosphorus treated zeolite.

11. The method of claim 1, wherein the binder further comprises calcium, alumina, silica aluminate, or a combination thereof.

12. The method of claim 1 wherein the contacting occurs at ambient pressure.

13. The method of claim 1 wherein the contacting occurs at a pressure of about 1 psig to about 20 psig.

14. The method of claim 1 wherein the contacting occurs at a temperature of about 600° F. to about 1,200° F.

15. The method of claim 1 further comprising steaming the catalyst prior to contacting the first mixture of C4+ compounds with the catalyst.

16. The method of claim 15, wherein the steaming is performed at a temperature of about 800° F. to about 1200° F.

17. The method of claim 2, wherein the first mixture of C4+ compounds and/or the second mixture of C4+ compounds is diluted with steam.

18. The method of claim 17, wherein the first mixture of C4+ compounds and/or the second mixture of C4+ compounds is diluted with about 20 to about 35% by weight of steam, based on the weight of the first mixture of C4+ compounds and/or the second mixture of C4+ compounds, respectively.

* * * * *

UNITED STATES PATENT AND TRADEMARK OFFICE
CERTIFICATE OF CORRECTION

PATENT NO. : 10,513,472 B2
APPLICATION NO. : 16/165603
DATED : December 24, 2019
INVENTOR(S) : David W. Leyshon It is certified that error appears in the above-identified patent and that said Letters Patent is hereby corrected as shown below:

In the Claims

Column 8      Line 3      Delete "1:8-16:20," and insert --1:8-16:20-28,--

Signed and Sealed this
Eighteenth Day of August, 2020

Andrei Iancu
*Director of the United States Patent and Trademark Office*